(12) United States Patent
Li et al.

(10) Patent No.: US 9,630,912 B2
(45) Date of Patent: Apr. 25, 2017

(54) SHIKONIN, ALKANNIN; AND RACEMIC PARENT NUCLEUS CABONYL OXIME DERIVATIVES AND APPLICATIONS THEREOF

(71) Applicant: SHANGHAI JIAO TONG UNIVERSITY, Shanghai (CN)

(72) Inventors: Shaoshun Li, Shanghai (CN); Rubing Wang, Shanghai (CN); Xiaogang Zheng, Shanghai (CN); Xu Zhang, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 0 days.

(21) Appl. No.: 14/759,024

(22) PCT Filed: Jun. 25, 2013

(86) PCT No.: PCT/CN2013/077849
§ 371 (c)(1),
(2) Date: Jul. 2, 2015

(87) PCT Pub. No.: WO2014/110889
PCT Pub. Date: Jul. 24, 2014

(65) Prior Publication Data
US 2015/0344415 A1    Dec. 3, 2015

(30) Foreign Application Priority Data

Jan. 16, 2013 (CN) .......................... 2013 1 0016436
Feb. 4, 2013 (CN) .......................... 2013 1 0044118

(51) Int. Cl.
C07C 251/34 (2006.01)
C07C 251/46 (2006.01)
C07C 249/08 (2006.01)
C07D 213/79 (2006.01)
C07D 333/40 (2006.01)
A61K 31/15 (2006.01)
A61K 31/222 (2006.01)

(52) U.S. Cl.
CPC ............ *C07C 251/34* (2013.01); *A61K 31/15* (2013.01); *A61K 31/222* (2013.01); *C07C 249/08* (2013.01); *C07C 251/46* (2013.01); *C07D 213/79* (2013.01); *C07D 333/40* (2013.01)

(58) Field of Classification Search
None
See application file for complete search history.

(56) References Cited

FOREIGN PATENT DOCUMENTS

| CN | 101139287 | 3/2008 |
|---|---|---|
| CN | 101863766 | 10/2010 |
| CN | 102557914 | 7/2012 |
| EP | 2116527 | 11/2009 |
| WO | 2005095330 | 10/2005 |

OTHER PUBLICATIONS

Li Shaoshun et al.Cryptotanshinone suppresses androgen receptor-mediated growth in androgen dependent and castration resistant prostate cancer cells.Cancer Letters. 2012, vol. 316, No. 1.

*Primary Examiner* — Timothy R Rozof

(57) ABSTRACT

A structural formula of a shikonin naphthazarin parent nucleus hydroxyl methylation carbonyl oxime derivative is shown in Formula (I) or (II); a structural formula of an alkannin naphthazarin parent nucleus hydroxyl methylation carbonyl oxime derivative is shown in Formula (III) or (IV); and a structural formula of a racemic shikonin naphthazarin parent nucleus hydroxyl methylation carbonyl oxime derivative is shown in Formula (V) or (VI), wherein R1 is alkane, olefin, arene, or substituting arene comprising 1 to 6 carbon atoms; and R2 is alkane, olefin, arene, or substituting arene comprising 1 to 6 carbon atoms or is H. The shikonin, alkannin, and racemic oxime derivatives of the present invention have novel structures, and in-vitro experiments show that the present invention has good growth inhibitory activity against tumor cells and can be used in tumor treatment.

9 Claims, 3 Drawing Sheets

SHIKONIN, ALKANNIN; AND RACEMIC PARENT NUCLEUS CABONYL OXIME DERIVATIVES AND APPLICATIONS THEREOF

CROSS REFERENCE OF RELATED APPLICATION

This is a U.S. National Stage under 35 U.S.C. 371 of the International Application PCT/CN2013/077849, filed Jun. 25, 2013, which claims priority under 35 U.S.C. 119(a-d) to CN 201310016436.5, filed Jan. 16, 2013, and CN 201310044118.X, filed Feb. 4, 2013.

BACKGROUND OF THE PRESENT INVENTION

Field of Invention

The present invention relates to a series of shikonin, alkannin and racemic parent nucleus hydroxyl methylation carbonyl oxime derivatives and their application in the medicine field.

Description of Related Arts

Alkannin (S-isomer) and shikonin (R-isomer) were extracted and identified from the roots of *Alkanna tinctoria* in Europe and *Lithospermum erythrorhizon* in the Orient as a pair of enantiomers, respectively. They also exhibit multiple biological properties including anti-inflammatory, aiding wound healing, antibacterial, antiviral, antithrombotic, antithyroid, immunoregulatory, hypoglycemic, hepatoprotective activities. There has been increasing interest in these compounds over the past few decades given their potent anticancer activities. So far, most modifications have focused on the hydroxyl group in the side chain and the naphthazarin ring. On the one hand, the naphthazarin ring was kept while the hydroxyl group in the side chain was modified (CN142011, CN1112363). On the other hand, the modification of naphthazarin ring was performed, including the alkylation or acetylation to synthesize the corresponding shikonin and alkannin derivatives (201010046435.2, 201010209926.3, 201210021929.3 and 201010065488.7).

SUMMARY OF THE PRESENT INVENTION

An object of the present invention is to provide shikonin, alkannin and racemic parent nucleus hydroxyl methylation carbonyl oxime derivatives and applications thereof The compounds in the present invention have novel structures, are easy to be prepared and have good growth inhibitory activity against tumor cells in vitro.

The present invention is realized by the following technology:

the present invention involves shikonin, alkannin and racemic parent nucleus hydroxyl methylation carbonyl oxime derivatives;

wherein, a structural formula of a shikonin naphthazarin parent nucleus hydroxyl methylation carbonyl oxime derivative is shown in Formula (I) or (II);

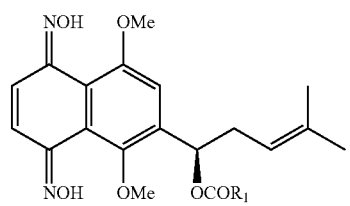

(I)

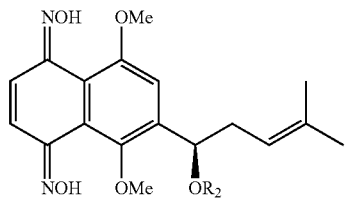

(II)

a structural formula of a alkain naphthazarin parent nucleus hydroxyl methylation carbonyl oxime derivative is shown in Formula (III) or (IV);

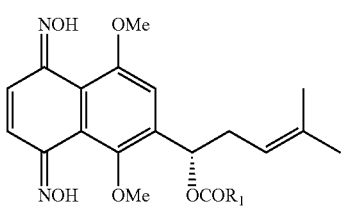

(III)

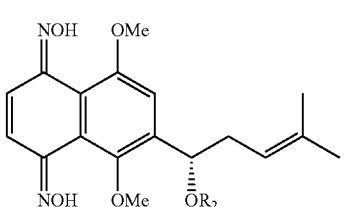

(IV)

a structural formula of a racemic naphthazarin parent nucleus hydroxyl methylation carbonyl oxime derivative is shown in Formula (V) or (VI);

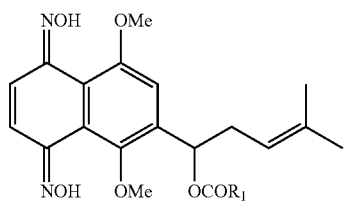

(V)

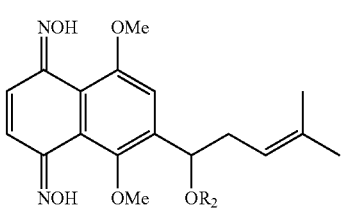

(VI)

wherein, $R_1$ is alkane, olefin, arene, or substituting arene comprising 1 to 6 carbon atoms; and $R_2$ is alkane, olefin, arene or substituting arene comprising 1-6 carbon atoms, or is H.

Preferably, $R_1$ in the above shikonin, alkannin and racemic naphthazarin parent nucleus hydroxyl methylation carbonyl oxime derivative is methyl, isopropyl, isobutyl, 2-hydroxyl-2-methylpropyl, phenyl, 2-fluorophenyl, 4-fluorophenyl, 1-methylethylene, 2-clorophenyl, 4-clorophenyl, 4-methoxyphenyl, ethylene, 2-thiophenyl, 4-nitrophenyl or 2-pyridyl; $R_2$ is hydrogen, methyl, ethyl or isopentyl.

The present invention also involves a preparation method of above shikonin, alkannin and racemic naphthazarin parent nucleus hydroxyl methylation carbonyl oxime derivative. For the shikonin naphthazarin parent nucleus hydroxyl methylation carbonyl oxime derivatives shown as Formula (I) or (II), the preparation method comprises following steps of:

(A) using 1,4,5,8-tetramethoxyshikonin as starting material, in the presence of DCC and DMAP, reacting the hydroxyl group on the side chain of 1,4,5,8-tetramethoxyshikonin with carboxylic acid to provide ester derivatives, or in the presence of NaH suspended in DMF, reacting the hydroxyl group on the side chain of 1,4,5,8-tetramethoxyshikonin with alkyl halides to provide ether derivatives; and (B) oxidizing and demethylating the ester derivatives or ether derivatives mentioned above to provide dimethyl dicarbonyl compounds which then coupled with hydroxylamine hydrochloride in the presence of anhydrous pyridine to form the ester or ether derivatives of shikonin naphthazarin parent nucleus hydroxyl methylation carbonyl oxime.

Preferably, in the step (A), the molar ratio of 1,4,5,8-tetramethoxyshikonin, DCC and carboxylic acid is 1:1.5:1.2-1:5:2; the molar ratio of 1,4,5,8-tetramethoxyshikonin, NaH and alkyl halide is 1:3:1.5-1:6:4; in the step (B), the molar ratio of ester derivatives or ether derivatives and CAN is 1:5-1:10, the molar ratio of oxidized product of ester derivatives or ether derivatives, hydroxylamine hydrochloride and anhydrous pyridine is 1:2.2:3-1:5:8.

The present invention also involves a preparation method of above shikonin, alkannin and racemic naphthazarin parent nucleus hydroxyl methylation carbonyl oxime derivative. For the alkannin naphthazarin parent nucleus hydroxyl methylation carbonyl oxime derivatives shown as Formula (III) or (IV), the preparation method comprises following steps of:

(A) using 1,4,5,8-tetramethoxyalkannin as starting material, in the presence of DCC and DMAP, reacting the hydroxyl group on the side chain of 1,4,5,8-tetramethoxyalkannin with carboxylic acid to provide ester derivatives, or in the presence of NaH suspended in DMF, reacting the hydroxyl group on the side chain of 1,4,5,8-tetramethoxyalkannin with alkyl halides to provide ether derivatives; and (B) oxidizing and demethylating the ester derivatives or ether derivatives mentioned above to provide dimethyl dicarbonyl compounds which then coupled with hydroxylamine hydrochloride in the presence of anhydrous pyridine to form the ester or ether derivatives of alkannin naphthazarin parent nucleus hydroxyl methylation carbonyl oxime.

Preferably, in the step (A), the molar ratio of 1,4,5,8-tetramethoxyalkannin, DCC and carboxylic acid is 1:1.5:1.2-1:5:2; the molar ratio of 1,4,5,8-tetramethoxyalkannin, NaH and alkyl halide is 1:3:1.5-1:6:4; in the step (B), the molar ratio of ester derivatives or ether derivatives and CAN is 1:5-1:10, the molar ratio of oxidized product of ester derivatives or ether derivatives, hydroxylamine hydrochloride and anhydrous pyridine is 1:2.2:3-1:5:8.

The present invention also involves a preparation method of above shikonin, alkannin and racemic naphthazarin parent nucleus hydroxyl methylation carbonyl oxime derivative. For the racemic naphthazarin parent nucleus hydroxyl methylation carbonyl oxime derivatives shown as Formula (V) or (VI), the preparation method comprises following steps of:

(A) using (±)1,4,5,8-tetramethoxyshikonin as starting material, in the presence of DCC and DMAP, reacting the hydroxyl group on the side chain of (±)1,4,5,8-tetramethoxyshikonin with carboxylic acid to provide ester derivatives, or in the presence of NaH suspended in DMF, reacting the hydroxyl group on the side chain of (±)1,4,5,8-tetramethoxyshikonin with alkyl halides to provide ether derivatives; and (B) oxidizing and demethylating the ester derivatives or ether derivatives mentioned above to provide dimethyl dicarbonyl compounds which then coupled with hydroxylamine hydrochloride in the presence of anhydrous pyridine to form the ester or ether derivatives of racemic naphthazarin parent nucleus hydroxyl methylation carbonyl oxime.

Preferably, in the step (A), the molar ratio of (±)1,4,5,8-tetramethoxyshikonin, DCC and carboxylic acid is 1:1.5:1.2-1:5:2; the molar ratio of (±)1,4,5,8-tetramethoxyshikonin, NaH and alkyl halide is 1:3:1.5-1:6:4; in the step (B), the molar ratio of ester derivatives or ether derivatives and CAN is 1:5-1:10, the molar ratio of oxidized product of ester derivatives or ether derivatives, hydroxylamine hydrochloride and anhydrous pyridine is 1:2.2:3-1:5:8.

The present invention also involves the application of above shikonin, alkannin and racemic naphthazarin parent nucleus hydroxyl methylation carbonyl oxime derivative in the preparation of antitumor agents.

Compared with conventional technology, the present invention has following advantages:

1. The present invention acquired a series of novel shikonin, alkannin and racemic naphthazarin parent nucleus hydroxyl methylation carbonyl oxime derivative based on the modification of shikonin, alkannin and racemic naphthazarin parent nucleus hydroxyl methylation derivatives. The starting materials used in the present invention, 1,4,5,8-tetramethoxyshikonin and 1,4,5,8-tetramethoxyalkannin with high chiral purity (>99%), were prepared refer to the published patent of inventors (CN102399139A).

2. The key starting material, (±)1,4,5,8-tetramethoxyshikonin, used in the present invention was prepared in one step refer to the authorized patent of inventors (ZL200510025243.1). This synthetic method of racemic isomer is easier and low cost.

3. Shikonin, alkannin and racemic naphthazarin parent nucleus hydroxyl methylation carbonyl oxime derivative prepared in the present invention all show good and selective tumor cell growth inhibitory activities in vitro which indicate their application in the tumor treatment.

BRIEF DESCRIPTION OF THE DRAWINGS

These and other objectives, features, and advantages of the present invention will become apparent from the following detailed description, the accompanying drawings, and the appended claims.

DETAILED DESCRIPTION OF THE PREFERRED EMBODIMENT

Figure 1:
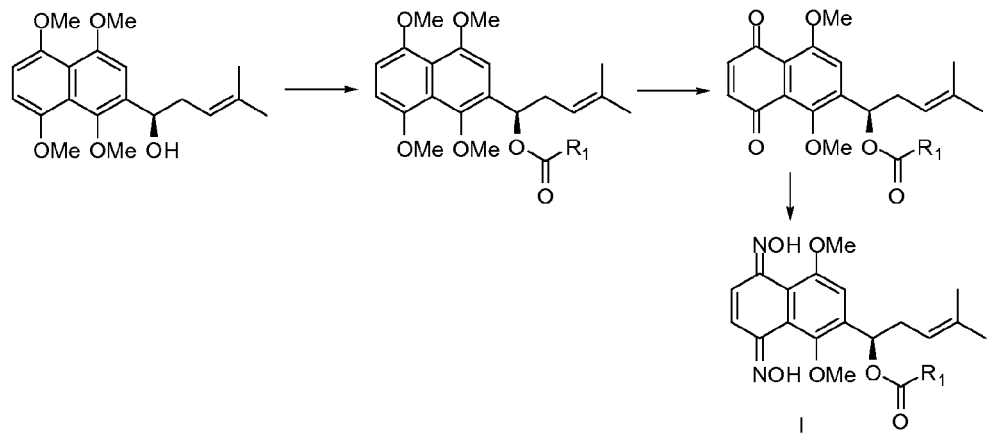
FIG. 1 illustrates a synthetic method of shikonin naphthazarin parent nucleus hydroxyl methylation carbonyl oxime ester derivative (Formula I).

One skilled in the art will understand that the embodiment of the present invention as shown in the drawings and described is exemplary only and not intended to be limiting. Its embodiments have been shown and described for the purposes of illustrating the functional and structural principles of the present invention and is subject to change without departure from such principles. Therefore, this invention includes all modifications encompassed within the spirit and scope.

Example 1

This example involves a series of shikonin and alkannin oxime compounds by way of the methylation of hydroxyl and the oximation of carbonyl groups on the naphthazarin ring. The general structures of these oxime compounds are shown as (I), (II), (III) and (IV):

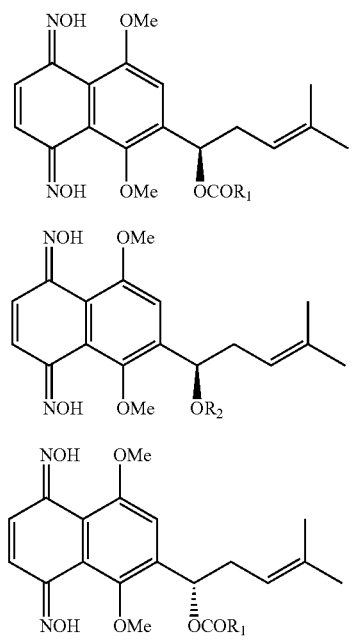

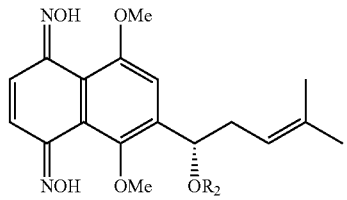

$R_1$ and $R_2$ were defined in table 1.

Figure 2:
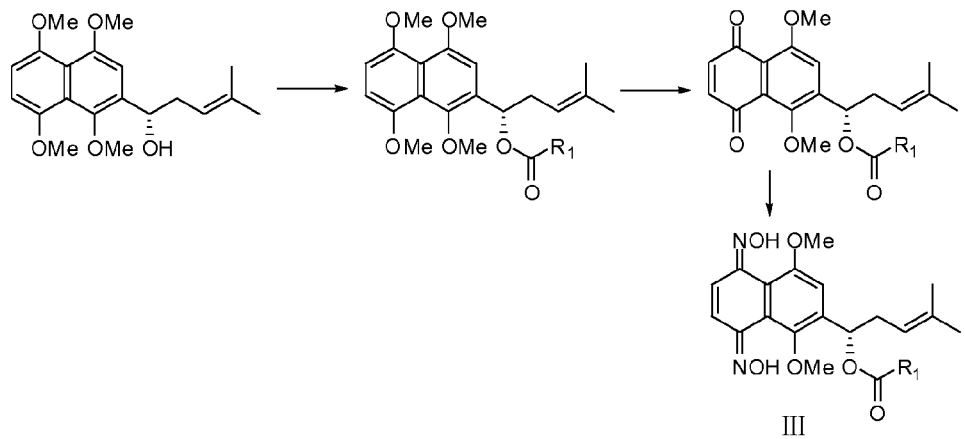
FIG. 2 illustrates a synthetic method of alkannin naphthazarin parent nucleus hydroxyl methylation carbonyl oxime ester derivative (Formula III).
Figure 6:
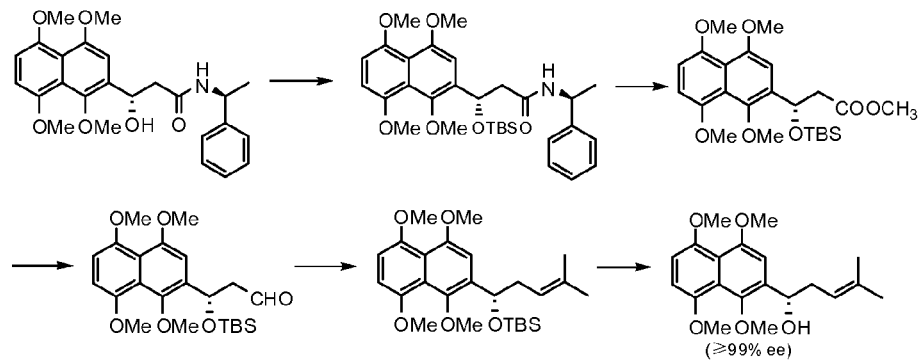
FIG. 6 illustrates a synthetic method of 1,4,5,8-tetramethoxyalkannin.

1. The Preparation of Ester Derivatives Named as Series of I and III;

The synthetic routes for compounds I and III were showed respectively in FIG. 1 and FIG. 2. The scheme for the synthesis of ester compounds I was regarded as FIG. 1; the scheme for the synthesis of ester compounds III was treated as FIG. 2. The general synthetic method for compounds I and III was given as follows, while 1,4,5,8-tetramethoxyshikonin and 1,4,5,8-tetramethoxyalkannin with high optical purity were used as starting material (shown in FIG. 6) (the synthetic methods of 1,4,5,8-tetramethoxyshikonin and 1,4,5,8-tetramethoxyalkannin were refer to the patent CN102399139A).

To (R)- or (S)-4-methyl-1-(1,4,5,8-tetramethxynaphthalen-2-yl)pent-3-en-1-ol in dry CH2Cl2 was added carboxylic acid (1.2-2 equivalent) (all the equivalent referred in this patent is molar equivalent), DCC (1.5-5 equivalent) and DMAP (0.1 equivalent) and the mixture was stirred for 2-12 h at room temperature. After the completion of reaction, the precipitate was removed by filtration. To the filtrate was added CAN (5-10 equivalent) in water (10 mL) and the mixture was stirred at 0-5° C. After 5-15 minutes, the reaction was extracted with DCM and the combined extracts were dried over anhydrous sodium sulfate and concentrated. The residue was purified by silica gel column chromatography to give yellow oily compounds. Stirring of obtained yellow oily compounds and hydroxylamine hydrochloride (2.2-5 equivalent) respectively in dry ethanol with the presence of pyridine (3-8 equivalent) produced ester oxime compounds I and III.

The specific synthesis of compounds I and III are as follows:

For the synthesis of I-1 and III-1, 1.5 equivalent DCC, 1.2 equivalent acetic acid, 5 equivalent CAN, 2.2 equivalent hydroxylamine hydrochloride and 3 equivalent pyridine were used. For the synthesis of I-2 and 111-2, 5 equivalent DCC, 2 equivalent 3-methylbutanoic acid, 10 equivalent CAN, 5 equivalent hydroxylamine hydrochloride and 8 equivalent pyridine were used. For the synthesis of I-3 and III-3, 3 equivalent DCC, 1.5 equivalent 3-hydroxy-3-methylbutanoicacid, 7 equivalent CAN, 3.5 equivalent hydroxylamine hydrochloride and 5 equivalent pyridine were used. For the synthesis of I-4-I-16 and III-4-III-16, 1.5 equivalent DCC, 1.2 equivalent carboxylic acid, 5 equivalent CAN, 2.2 equivalent hydroxylamine hydrochloride and 3 equivalent pyridine were used.

Figure 3:
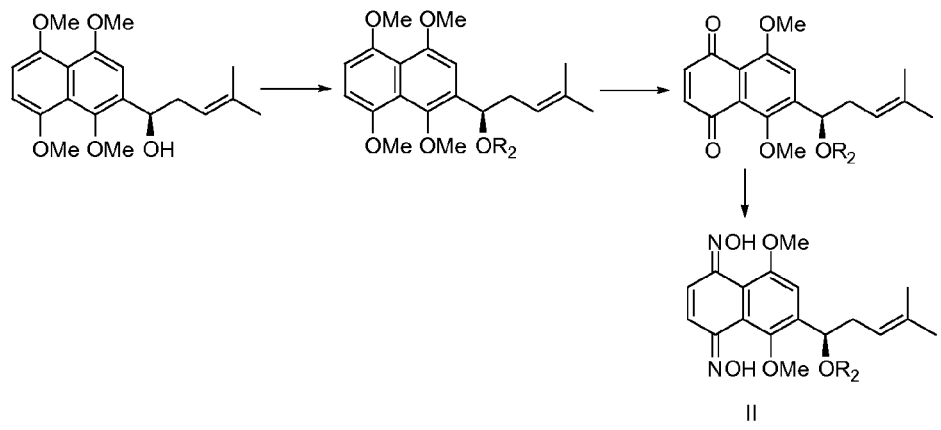
FIG. 3 illustrates a synthetic method of shikonin naphthazarin parent nucleus hydroxyl methylation carbonyl oxime ether derivative (Formula II).
Figure 4:
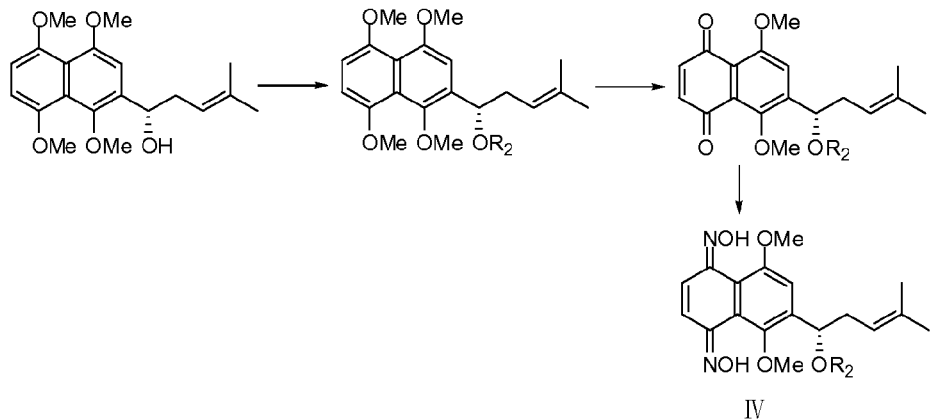
FIG. 4 illustrates a synthetic method of alkannin naphthazarin parent nucleus hydroxyl methylation carbonyl oxime ether derivative (Formula IV).
Figure 5:
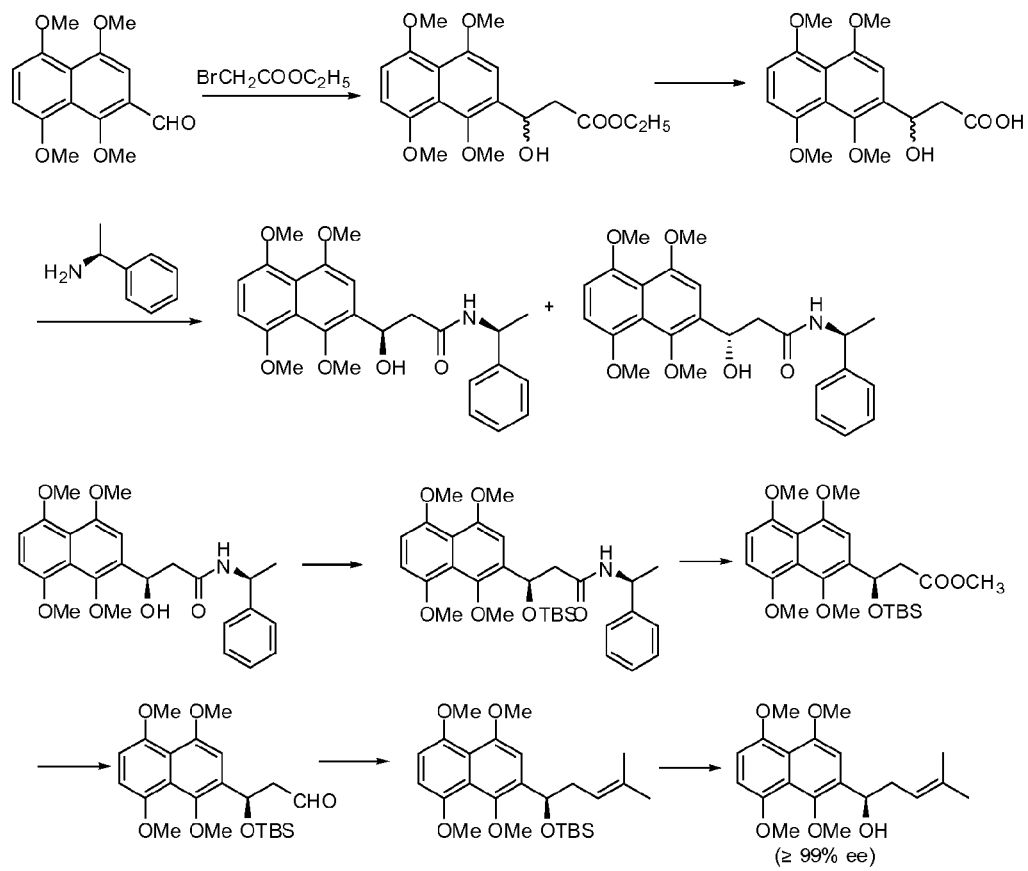
FIG. 5 illustrates a synthetic method of 1,4,5,8-tetramethoxyshikonin.

2. The Preparation of Ether Derivatives Named as Series of II and IV;

The scheme for the synthesis of ether compounds II was regarded as FIG. 3. The scheme for the synthesis of ether compounds IV was treated as FIG. 4. The general synthetic method for compounds II and IV was given as follows. The synthesis of high optical purity 1,4,5,8-tetramethoxyshikonin was shown in FIG. 5 and 1,4,5,8-tetramethoxyalkannin shown in FIG. 6.

To a cooled solution of (R)- or (S)-4-methyl-1-(1,4,5,8-tetramethoxynaphthalen-2-yl) pent-3-en-1-ol in dry DMF was added NaH (3-6 equivalent) and the mixture was stirred for 0.5 h at 0° C. Then alkyl halide (1.5-4 equivalent) was added and the reaction mixture was allowed to stir at room temperature for 12-24 h. After the completion of the reaction, the reaction was extracted with ethyl acetate and the extracts were concentrated. The residue was dissolved in DCM and a solution of CAN (5-10equivalent) in water was added and stirred for 5-15 minutes at 0° C. Then the organic phase was extracted with DCM and purified by silica gel column chromatography to collect yellow oily compounds, which were converted into ether oxime compounds in series II and IV by the condensation reaction with hydroxylamine hydrochloride (2.2-5 equivalent) in dry ethanol with the presence of pyridine (3-8 equivalent).

For the synthesis of II-1, 6 equivalent CAN, 3 equivalent hydroxylamine hydrochloride and 5 equivalent pyridine were used. For the synthesis of II-2, 6 equivalent NaH, 4 equivalent iodomethane, 10 equivalent CAN, 5 equivalent hydroxylamine hydrochloride and 8 equivalent pyridine were used. For the synthesis of II-3, 4 equivalent NaH, 2 equivalent bromoethane, 5 equivalent CAN, 2.2 equivalent hydroxylamine hydrochloride and 4.5 equivalent pyridine were used. For the synthesis of II-4, 3 equivalent NaH, 1.5 equivalent 1-bromo-3-methylbutane, 8 equivalent CAN, 4 equivalent hydroxylamine hydrochloride and 6 equivalent pyridine were used.

For the synthesis of IV-1, 6 equivalent CAN, 3 equivalent hydroxylamine hydrochloride and 5 equivalent pyridine were used. For the synthesis of IV-2, 6 equivalent NaH, 4 equivalent iodomethane, 10 equivalent CAN, 5 equivalent hydroxylamine hydrochloride and 8 equivalent pyridine were used. For the synthesis of IV-3, 4 equivalent NaH, 2 equivalent bromoethane, 5 equivalent CAN, 2.2 equivalent hydroxylamine hydrochloride and 4 equivalent pyridine were used. For the synthesis of IV-4, 3 equivalent NaH, 1.5 equivalent 1-bromo-3-methylbutane, 7.5 equivalent CAN, 7.5 equivalent hydroxylamine hydrochloride and 8 equivalent pyridine were used.

3. The Spectral Characterization of Compounds I-IV (R)-1-((5E,8E)-5,8-bis(hydroxyimino)-1,4-dimethoxy-5,8-dihydronaphthalen-2-yl)-4-methylpent-3-en-1-yl acetate (I-1): yield 84%, $^1$H NMR (300 MHz, DMSO): δ=12.06 (s, 2H, $H_{NOH}$), 7.36 (s, 2H, $H_{Quin}$), 7.02 (s, 1H, $H_{Ar}$), 6.00 (t, J=6.3 Hz, 1H, ArCH—), 5.10 (t, J=6.3 Hz, 1H, —CH=), 3.78 (s, 3H, ArOCH$_3$), 3.62 (s, 3H, ArOCH$_3$), 2.47 (d, J=1.5 Hz, 2H, —CH$_2$—), 2.06 (s, 3H, —COCH$_3$), 1.62 (s, 3H, —CH$_3$), 1.52 (s, 3H, —CH$_3$). ESI-MS m/z 411 [M+Na]$^+$.

The yield and $^1$H NMR of (3)-1-((5E,8E)-5,8-bis(hydroxyimino)-1,4-dimethoxy-5,8-dihydronaphthalen-2-yl)-4-methylpent-3-en-1-yl acetate's yield and $^1$H NMR data (III-1) were the same as I-1.

(R)-1-((5E,8E)-5,8-bis(hydroxyimino)-1,4-dimethoxy-5,8-dihydronaphthalen-2-yl)-4-methylpent-3-en-1-yl 3-methylbut-2-enoate (I-2): yield 79%, $^1$H NMR (300 MHz, DMSO): δ=12.05 (s, 2H, $H_{NOH}$), 7.35 (s, 2H, $H_{Quin}$), 6.99 (s, 1H, $H_{Ar}$), 6.03 (t, J=6.2 Hz, 1H, ArCH—), 5.77 (s, 1H, —COCH=C—), 5.09 (s, 1H, —CH$_2$CH=C—), 3.73 (s, 3H, ArOCH$_3$), 3.63 (s, 3H, ArOCH$_3$), 2.47(t, J=1.8 Hz, 2H, —CH$_2$—), 2.07 (s, 3H, —CH=CCH$_3$), 1.85 (s, 3H, —CH=CCH$_3$), 1.59 (s, 3H, —CH$_3$), 1.51 (s, 3H, —CH$_3$). ESI-MS m/z 451 [M+Na]$^+$.

The yield and $^1$H NMR of (R)-1-((5E,8E)-5,8-bis(hydroxyimino)-1,4-dimethoxy-5,8-dihydronaphthalen-2-yl)-4-methylpent-3-en-1-yl 3-methylbut-2-enoate (III-2) were the same as I-2.

(R)-1-((5E,8E)-5,8-bis(hydroxyimino)-1,4-dimethoxy-5,8-dihydronaphthalen-2-yl)-4-methylpent-3-en-1-yl 3-hydroxy-3-methylbutanoate (I-3): yield 78%, $^1$H NMR (300 MHz, DMSO): δ=12.08 (s, 2H, $H_{NOH}$), 7.38 (s, 2H, $H_{Quin}$), 7.10 (s, 1H, $H_{Ar}$), 6.00 (t, J=6.6 Hz, 1H, ArCH—), 5.18-5.14 (m, 1H, —CH=), 4.63 (s, 1H, —CHOH), 3.78 (s, 3H, ArOCH$_3$), 3.66 (s, 3H, ArOCH$_3$), 2.54-2.43 (m, 4H, —CH$_2$—), 1.64 (s, 3H, —CH=CCH$_3$), 1.54 (s, 3H, —CH=CCH$_3$), 1.23 (s, 3H, —CH$_3$), 1.18 (s, 3H, —CH$_3$). ESI-MS m/z 469 [M+Na]$^+$.

The yield and $^1$H NMR of of (S)-1-((5E,8E)-5,8-bis(hydroxyimino)-1,4-dimethoxy-5,8-dihydronaphthalen-2-yl)-4-methylpent-3-en-1-yl 3-hydroxy-3-methylbutanoate (III-3) were the same as 1-3.

(R)-1-((5E,8E)-5,8-bis(hydroxyimino)-1,4-dimethoxy-5,8-dihydronaphthalen-2-yl)-4-methylpent-3-en-1-yl isobutyrate (I-4): yield 79%, $^1$H NMR (400 MHz, DMSO): δ=12.08 (s, 2H, $H_{NOH}$), 7.38 (s, 2H, $H_{Quin}$), 7.02 (s, 1H, $H_{Ar}$), 6.01 (t, J=6.6 Hz, 1H, ArCH—), 5.14 (s, 1H, —CH=), 3.78 (s, 3H, ArOCH$_3$), 3.66 (s, 3H, ArOCH$_3$), 2.67-2.50 (m, 3H, —COCH— and =CCH$_2$—), 1.66 (s, 3H, —CH=CCH$_3$), 1.56 (s, 3H, —CH=CCH$_3$), 1.13 (s, 3H, —CH$_3$), 1.12 (s, 3H, —CH$_3$). ESI-MS m/z 417 [M+H]$^+$.

The yield and $^1$H NMR of (S)-1-((5E,8E)-5,8-bis(hydroxyimino)-1,4-dimethoxy-5,8-dihydronaphthalen-2-yl)-4-methylpent-3-en-1-yl isobutyrate (III-4) were the same as I-4.

(R)-1-((5E,8E)-5,8-bis(hydroxyimino)-1,4-dimethoxy-5,8-dihydronaphthalen-2-yl)-4-methylpent-3-en-1-yl 3-methylbutanoate (I-5): yield 80%, $^1$H NMR (300 MHz, DMSO): δ=12.07 (s, 2H, $H_{NOH}$), 7.37 (s, 2H, $H_{Quin}$), 7.02 (s, 1H, $H_{Ar}$), 6.04 (t, J=7.2 Hz, 1H, ArCH—), 5.14 (d, J=6.0 Hz, 1H, —CH=), 3.77 (s, 3H, ArOCH$_3$), 3.65 (s, 3H, ArOCH$_3$), 2.48 (s, 2H, —CH$_2$—), 2.25 (d, J=7.2 Hz, 2H, —CH$_2$—), 2.0 (m, 1H, —CH—), 1.62 (s, 3H, —CH=CCH$_3$), 1.54 (s, 3H, —CH=CCH$_3$), 0.89 (s, 3H, —CH$_3$), 0.87 (s, 3H, —CH$_3$). ESI-MS m/z 453 [M +Na]$^+$.

The yield and $^1$H NMR of (S)-1-(5E,8E)-5,8-bis(hydroxyimino)-1,4-dimethoxy-5,8-dihydronaphthalen-2-yl)-4-methylpent-3-en-1-yl 3-methylbutanoate (III-5) were the same as I-5.

(R)-1-((5E,8E)-5,8-bis(hydroxyimino)-1,4-dimethoxy-5,8-dihydronaphthalen-2-yl)-4-methylpent-3-en-1-yl propionate (I-6): yield 86%, $^1$H NMR (400 MHz, DMSO): δ=12.08 (s, 2H, $H_{NOH}$), 7.38 (s, 2H, $H_{Quin}$), 7.03 (s, 1H, $H_{Ar}$), 6.04 (t, J=6.0 Hz, 1H, ArCH—), 5.13 (t, J=6.4 Hz, 1H, —CH=), 3.79 (s, 3H, ArOCH$_3$), 3.66 (s, 3H, ArOCH$_3$), 2.50-2.37 (m, 4H, —CH$_2$—), 1.64 (s, 3H, —CH=CCH$_3$), 1.55 (s, 3H, —CH=CCH$_3$), 1.05 (t, J=7.2 Hz, 3H, —CH$_3$). ESI-MS m/z 403 [M+H]$^+$.

The yield and $^1$H NMR of (S)-1-((5E,8E)-5,8-bis(hydroxyimino)-1,4-dimethoxy-5,8-dihydronaphthalen-2-yl)-4-methylpent-3-en-1-yl propionate (III-6) were the same as I-6.

(R)-1-((5E,8E)-5,8-bis(hydroxyimino)-1,4-dimethoxy-5,8-dihydronaphthalen-2-yl)-4-methylpent-3-en-1-yl methacrylate (I-7): yield 78%, $^1$H NMR (400 MHz, DMSO): δ=12.09 (s, 2H, $H_{NOH}$), 7.39 (s, 2H, $H_{Quin}$), 7.06 (s, 1H, $H_{Ar}$), 6.16 (s, 1H, —C=CH$_2$), 6.10 (dd, J=7.2, 5.6 Hz, 1H, C=CH$_2$), 5.74 (s, 1H, ArCH—), 5.14 (t, 1H, J=6.8 Hz, —CH$_2$C=), 3.77 (s, 3H, ArOCH$_3$), 3.67 (s, 3H, ArOCH$_3$), 2.62-2.53 (m, 2H, —CH$_2$—), 1.92 (s, 3H, —CH$_2$=CCH$_3$), 1.64 (s, 3H, —CH$_3$), 1.56 (s, 3H, —CH$_3$). ESI-MS m/z 415 [M+H]$^+$.

The yield and ¹H NMR of (S)-1-(5E,8E)-5,8-bis(hydroxyimino)-1,4-dimethoxy-5,8-dihydronaphthalen-2-yl)-4-methylpent-3-en-1-yl methacrylate (III-7) were the same as 1-7.

(R)-1-((5E,8E)-5,8-bis(hydroxyimino)-1,4-dimethoxy-5,8-dihydronaphthalen-2-yl)-4-methylpent-3-en-1-yl benzoate (I-8): yield 79%, ¹H NMR (400 MHz, DMSO): δ=12.10 (s, 2H, $H_{NOH}$), 8.06 (d, J=6.8 Hz, 2H, $H_{Quin}$), 7.70-7.39 (m, 5H, $H_{Ar}$), 7.19 (s, 1H, $H_{Ar}$), 6.30 (t, J=6.0 Hz, 1H, ArCH—), 5.20 (s, 1H, =CH—), 3.75 (s, 3H, ArOCH₃), 3.71 (s, 3H, ArOCH₃), 2.72-2.63 (m, 2H, —CH₂—), 1.64 (s, 3H, —CH₃), 1.59 (s, 3H, —CH₃). ESI-MS m/z 451 [M+H]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl benzoate (III-8) were the same as I-8.

(R)-1-((5E,8E)-5,8-bis(hydroxyimino)-1,4-dimethoxy-5,8-dihydronaphthalen-2-yl)-4-methylpent-3-en-1-yl 2-fluorobenzoate (I-9): yield 77%, ¹H NMR (400 MHz, DMSO): δ=12.10 (s, 2H, $H_{NOH}$), 7.96 (dd, J=7.6, 6.4 Hz, 1H, $H_{Ar}$), 7.71-7.68 (m, 1H, $H_{Ar}$), 7.41-7.35 (m, 4H, $H_{Ar}$ and $H_{Quin}$), 7.18 (s, 1H, ArH), 6.31 (t, J=5.6 Hz, 1H, ArCH—), 5.20 (t, J=6.8 Hz, 1H, =CH—), 3.76 (s, 3H, ArOCH₃), 3.71 (s, 3H, ArOCH₃), 2.69-2.60 (m, 2H, —CH₂—), 1.64 (s, 3H, —CH₃), 1.55 (s, 3H, —CH₃). ESI-MS m/z 469 [M+H]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl 2-fluorobenzoate (III-9) were the same as I-9.

(R)-1-((5E,8E)-5,8-bis(hydroxyimino)-1,4-dimethoxy-5,8-dihydronaphthalen-2-yl)-4-methylpent-3-en-1-yl 4-fluorobenzoate(I-10): yield 79%, ¹H NMR (400 MHz, DMSO): δ=12.10 (s, 2H, $H_{NOH}$), 8.12 (dd, J=8.4, 5.6 Hz, 2H, $H_{Quin}$), 7.39-7.35 (m, 4H, $H_{Ar}$), 7.19 (s, 1H, $H_{Ar}$), 6.31-6.28 (m, 1H, ArCH—), 5.20 (t, J=2.0 Hz, 1H, =CH—), 3.76 (s, 3H, ArOCH₃), 3.70 (s, 3H, ArOCH₃), 2.74-2.61 (m, 2H, —CH₂—), 1.63 (s, 3H, —CH₃), 1.58 (s, 3H, —CH₃). ESI-MS m/z 469 [M+H]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl 4-fluorobenzoate(III-10) were the same as I-10.

(R)-1-((5E,8E)-5,8-bis(hydroxyimino)-1,4-dimethoxy-5,8-dihydronaphthalen-2-yl)-4-methylpent-3-en-1-yl 2-chlorobenzoate (I-11): yield 78%, ¹H NMR (400 MHz, DMSO): δ=12.11 (s, 2H, $H_{NOH}$), 7.87 (d, J=7.6 Hz, 1H, $H_{Ar}$), 7.60 (d, J=3.6 Hz, 2H, $H_{Ar}$), 7.52-7.48 (m, 1H, $H_{Ar}$), 7.40 (s, 2H, $H_{Quin}$), 7.18 (s, 1H, $H_{Ar}$), 6.30 (t, J=5.6 Hz, 1H, ArCH—), 5.21 (s, 1H, =CH—), 3.77 (s, 3H, ArOCH₃), 3.71 (s, 3H, ArOCH₃), 2.69-2.63 (m, 2H, —CH₂—), 1.65 (s, 3H, —CH₃), 1.56 (s, 3H, —CH₃). ESI-MS m/z 485 [M+H]⁺.

The yield and ¹H NMR of (S)-1-(5E,8E)-5,8-bis(hydroxyimino)-1,4-dimethoxy-5,8-dihydronaphthalen-2-yl)-4-methylpent-3-en-1-yl 2-chlorobenzoate (III-11) were the same as I-11.

(R)-1-((5E,8E)-5,8-bis(hydroxyimino)-1,4-dimethoxy-5,8-dihydronaphthalen-2-yl)-4-methylpent-3-en-1-yl 4-chlorobenzoate (I-12): yield 81%, ¹H NMR (400 MHz, DMSO): δ=12.10 (s, 2H, $H_{NOH}$), 8.07 (d, J=8.4 Hz, 2H, $H_{Ar}$), 7.62 (d, J=8.4 Hz, 2H, $H_{Ar}$), 7.39 (s, 2H, $H_{Quin}$), 7.18 (s, 1H, $H_{Ar}$), 6.30 (t, J=5.6 Hz, 1H, ArCH—), 5.19 (s, 1H, =CH—), 3.76 (s, 3H, ArOCH₃), 3.70 (s, 3H, ArOCH₃), 2.72-2.63 (m, 2H, —CH₂—), 1.64 (s, 3H, —CH₃), 1.59 (s, 3H, —CH₃). ESI-MS m/z 485 [M+H]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl 4-chlorobenzoate (III-12) were the same as I-12.

(R)-1-((5E,8E)-5,8-bis(hydroxyimino)-1,4-dimethoxy-5,8-dihydronaphthalen-2-yl)-4-methylpent-3-en-1-yl 4-methoxybenzoate (I-13): yield 85%, ¹H NMR (400 MHz, DMSO): δ=12.10 (s, 2H, $H_{NOH}$), 8.01 (d, J=4.8 Hz, 2H, $H_{Ar}$), 7.39 (s, 2H, $H_{Quin}$), 7.07 (d, J=8.8 Hz, 2H, $H_{Ar}$), 6.26 (t, J=5.6 Hz, 1H, ArCH—), 5.20 (s, 1H, =CH—), 3.84 (s, 3H, ArOCH₃), 3.74 (s, 3H, ArOCH₃), 3.70 (s, 3H, ArOCH₃), 2.70-2.59 (m, 2H, —CH₂—), 1.64 (s, 3H, —CH₃), 1.58 (s, 3H, —CH₃). ESI-MS m/z 481 [M+H]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl 4-methoxybenzoate (III-13) were the same as I-13.

(R)-1-((5E,8E)-5,8-bis(hydroxyimino)-1,4-dimethoxy-5,8-dihydronaphthalen-2-yl)-4-methylpent-3-en-1-yl 4-nitrobenzoate (I-14): yield 82%, ¹H NMR (400 MHz, DMSO): δ=12.11 (s, 2H, $H_{NOH}$), 8.12 (d, J=24.8 Hz, 4H, $H_{Ar}$), 7.39 (s, 2H, $H_{Quin}$), 7.21 (s, 1H, $H_{Ar}$), 6.34 (s, 1H, ArCH—), 5.20 (s, 1H, =CH—), 3.77 (s, 3H, ArOCH₃), 3.71 (s, 3H, ArOCH₃), 2.75-2.68 (m, 2H, —CH₂—), 1.63 (s, 3H, —CH₃), 1.59 (s, 3H, —CH₃). ESI-MS m/z 496 [M+H]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl 4-nitrobenzoate (III-14) were the same as I-14.

(R)-1-((5E,8E)-5,8-bis(hydroxyimino)-1,4-dimethoxy-5,8-dihydronaphthalen-2-yl)-4-methylpent-3-en-1-yl picolinate (I-15): yield 83%, ¹H NMR (400 MHz, DMSO): δ=12.11 (s, 2H, $H_{NOH}$), 8.76 (d, J=4.4 Hz, 1H, $H_{Py}$), 8.13 (d, J=8.0 Hz, 1H, $H_{Py}$), 8.04-8.00 (m, 1H, $H_{Py}$), 7.68-7.65 (m, 1H, $H_{Py}$), 7.39 (s, 2H, $H_{Quin}$), 7.22 (s, 1H, $H_{Ar}$), 6.32 (t, J=6.0 Hz, 1H, ArCH—), 5.20 (t, J=6.8 Hz, 1H, =CH—), 3.75 (s, 3H, ArOCH₃), 3.71 (s, 3H, ArOCH₃), 2.72-2.67 (m, 2H, —CH₂—), 1.63 (s, 3H, —CH₃), 1.59 (s, 3H, —CH₃). ESI-MS m/z 474 [M+Na]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl picolinate (III-15) were the same as I-15.

(R)-1-((5E,8E)-5,8-bis(hydroxyimino)-1,4-dimethoxy-5,8-dihydronaphthalen-2-yl)-4-methylpent-3-en-1-yl thiophene-2-carboxylate (I-16): yield 80%, ¹H NMR (400 MHz, DMSO): δ=12.11 (s, 2H, $H_{NOH}$), 7.97 (d, J=2.8 Hz, 1H, $H_{Thiophene}$), 7.90 (d, J=2.4 Hz, 1H, $H_{Thiophene}$), 7.39 (s, 2H, $H_{Quin}$), 7.24 (t, J=4.4 Hz, 1H, $H_{Thiophene}$), 7.15 (s, 1H, $H_{Ar}$), 6.26-6.23 (m, 1H, ArCH—), 5.18 (t, J=6.0 Hz, 1H, =CH—), 3.76 (s, 3H, ArOCH₃), 3.69 (s, 3H, ArOCH₃), 2.71-2.57 (m, 2H, —CH₂—), 1.64 (s, 3H, —CH₃), 1.59 (s, 3H, —CH₃). ESI-MS m/z 457 [M+H]⁺.

The yield and ¹H NMR of (S)-1-((5E,8E)-5,8-bis(hydroxyimino)-1,4-dimethoxy-5,8-dihydronaphthalen-2-yl)-4-methylpent-3-en-1-yl thiophene-2-carboxylate (III-16) were the same as I-16.

(1E,4E)-6-((R)-1-hydroxy-4-methylpent-3-en-1-yl)-5,8-dimethoxynaphthalene-1,4-dione dioxime(II-1): yield 87%, ¹H NMR(300 MHz, DMSO): δ=12.00 (s, 2H, $H_{NOH}$), 7.37 (s, 2H, $H_{Quin}$), 7.24 (s, 1H, $H_{Ar}$), 5.24 (s, 1H, =CH—), 4.92 (dd, J=7.5, 4.8 Hz, 1H, ArCH—), 3.78 (s, 3H, ArOCH₃), 3.58 (s, 3H, —OCH₃), 2.42-2.19 (m, 2H, —CH₂—), 1.64 (s, 3H, —CH₃), 1.52 (s, 3H, —CH₃). ESI-MS m/z 347 [M+H]⁺.

The yield and ¹H NMR of (1E,4E)-6-((S)-1-hydroxy-4-methylpent-3-en-1-yl)-5,8-dimethoxy naphthalene-1,4-dione dioxime(IV-1) were the same as II-1.

(1E,4E)-5,8-dimethoxy-6-((R)-1-methoxy-4-methylpent-3-en-1-yl)naphthalene-1,4-dione dioxime(II-2): yield 88%, $^1$H NMR(300 MHz, DMSO): δ=12.04 (s, 2H, H$_{NOH}$), 7.39 (s, 2H, H$_{Quin}$), 7.04 (s, 1H, H$_{Ar}$), 5.19 (t, J=6.9 Hz, 1H, —CH═), 4.59 (t, J=6.3 Hz, 1H, ArCH—), 3.78 (s, 3H, ArOCH$_3$), 3.59 (s, 3H, ArOCH$_3$), 3.17 (s, 3H, —OCH$_3$), 2.35 (t, J=6.3 Hz, 2H, —CH$_2$—), 1.63 (s, 3H, —CH$_3$), 1.49 (s, 3H, —CH$_3$). ESI-MS m/z 361 [M +H]$^+$.

The yield and $^1$H NMR of (1E,4E)-5,8-dimethoxy-6-((S)-1-methoxy-4-methylpent-3-en-1-yl) naphthalene-1,4-dione dioxime (IV-2) were the same as II-2.

(1E,4E)-6-((R)-1-ethoxy-4-methylpent-3-en-1-yl)-5,8-dimethoxynaphthalene-1,4-dione dioxime (II-3): yield 91%, $^1$H NMR (400 MHz, DMSO): δ=12.02 (s, 2H, H$_{NOH}$), 7.38 (s, 2H, H$_{Quin}$), 7.09 (s, 1H, H$_{Ar}$), 5.20 (t, J=5.6 Hz, 1H, ═CH—), 4.68 (t, J=6.8 Hz, 1H, ArCH—), 3.78 (s, 3H, ArOCH$_3$), 3.59 (s, 3H, ArOCH$_3$), 3.37-3.32 (m, 2H, —OCH$_2$CH$_3$), 2.36-2.35 (m, 2H, ═CHCH$_2$—), 1.64 (s, 3H, ═CCH$_3$), 1.50 (s, 3H, ═CCH$_3$), 1.20 (t, J=6.8 Hz, 3H, —CH$_3$). ESI-MS m/z 375 [M+H]$^+$.

The yield and $^1$H NMR of (1E,4E)-6-((S)-1-ethoxy-4-methylpent-3-en-1-yl)-5,8-dimethoxynaphthalene-1,4-dione dioxime (IV-3) were the same as II-3.

(1E,4E)-6-((R)-1-(isopentyloxy)-4-methylpent-3-en-1-yl)-5,8-dimethoxynaphthalene-1,4-dione dioxime (II-4): yield 81%, $^1$H NMR (400 MHz, DMSO): δ=12.02 (s, 2H, H$_{NOH}$), 7.38 (d, J=2.8 Hz, 2H, H$_{Quin}$), 7.08 (s, 1H, H$_{Ar}$), 5.21 (t, J=6.8 Hz, 1H, ═CH—), 4.65 (t, J=6.8 Hz, 1H, ═CH—), 3.78 (s, 3H, ArOCH$_3$), 3.60 (s, 3H, ArOCH$_3$), 3.31 (t, J=6.0 Hz, 2H, —CH$_2$O—), 2.35-2.32 (m, 2H, ═CHCH$_2$—), 1.75-1.68 (m, 1H, —CH(CH$_3$)$_2$), 1.64 (s, 3H, ═CCH$_3$), 1.51 (s, 3H, ═CCH$_3$), 1.44-1.38 (m, 2H, —CH$_2$CH(CH$_3$)$_2$), 0.87 (d, J=6.8 Hz, 3H, —CH$_3$), 0.82 (d, J=6.8 Hz, 3H, —CH$_3$). ESI-MS m/z 417 [M +H]$^+$.

The yield and $^1$H NMR of (1E,4E)-6-((S)-1-(isopentyloxy)-4-methylpent-3-en-1-yl)-5,8-dimethoxynaphthalene-1,4-dione dioxime (IV-4) were the same as II-4.

Example 2

The in vitro cytotoxicities of the prepared alkannin and shikonin oxime derivatives in example 1 were evaluated against MCF-7 (breast cancer), K562 (leukemia) and DU145 (prostate cancer) cells by the standard MTT assay. Antitumor potential of the forty compounds was displayed as IC$_{50}$ values that were calculated by linear regression analysis of the concentration-response curves afforded for each compound. The results are summarized in Table 1.

TABLE 1

In vitro inhibitory activity of compounds II and IV against DU145, MCF-7 and K562 cells

| Compds. | R (R$_1$ or R$_2$) | IC$_{50}$ (DU145) | IC$_{50}$ (MCF-7) | IC$_{50}$ (K562) |
|---|---|---|---|---|
| I-1 | methyl | 25.1 | 20.9 | 9.3 |
| I-2 | 3-methylbut-2-enyl | 11.3 | 6.0 | 1.4 |
| I-3 | 3-hydroxyisobutyl | 28.9 | 26 | 9.5 |
| I-4 | isopropyl | 10.2 | 4.9 | 3.3 |
| I-5 | isobutyl | 27.7 | 16.7 | 2.1 |
| I-6 | ethyl | 12.3 | 7.1 | 5.4 |
| I-7 | methylvinyl | 18.0 | 4.9 | 3.1 |
| I-8 | phenyl | 19.4 | 4.5 | 1.9 |
| I-9 | 2-fluorophenyl | 19.9 | 7.7 | 1.7 |
| I-10 | 4-fluorophenyl | 18.4 | 3.6 | 1.5 |
| I-11 | 2-chlorophenyl | 18.0 | 5.8 | 2.9 |
| I-12 | 4-chlorophenyl | 16.8 | 6.6 | 2.1 |
| I-13 | 4-methoxyphenyl | 16.3 | 6.3 | 2.5 |
| I-14 | 4-nitrophenyl | 19.7 | 3.9 | 2.6 |
| I-15 | pyridin-2-yl | 12.1 | 7.6 | 3.8 |
| I-16 | thiophen-2-yl | 16.9 | 5.7 | 2.0 |
| II-1 | hydrogen | 72.4 | 57.4 | 42.7 |
| II-2 | methyl | 32.4 | 30.2 | 21.1 |
| II-3 | ethyl | 17.1 | 15.7 | 17.1 |
| II-4 | isopentyl | 26.3 | 16.2 | 12.4 |
| III-1 | methyl | 17.1 | 8.1 | 5.3 |
| III-2 | 3-methylbut-2-enyl | 18.1 | 1.6 | 0.7 |
| III-3 | 3-hydroxyisobutyl | 32.8 | 8.2 | 4.7 |
| III-4 | isopropyl | 18.0 | 3.7 | 3.0 |
| III-5 | isobutyl | 19.3 | 7.5 | 0.7 |
| III-6 | ethyl | 20.6 | 3.1 | 3.7 |
| III-7 | methylvinyl | 19.5 | 2.4 | 2.6 |
| III-8 | phenyl | 16.9 | 2.8 | 1.6 |
| III-9 | 2-fluorophenyl | 14.3 | 1.8 | 1.5 |
| III-10 | 4-fluorophenyl | 17.0 | 1.5 | 1.3 |
| III-11 | 2-chlorophenyl | 16.8 | 1.7 | 1.3 |
| III-12 | 4-chlorophenyl | 21.4 | 2.4 | 1.3 |
| III-13 | 4-methoxyphenyl | 16.9 | 1.9 | 2.1 |
| III-14 | 4-nitrophenyl | 12.5 | 1.2 | 1.7 |
| III-15 | pyridin-2-yl | 20.7 | 6.3 | 3.6 |
| III-16 | thiophen-2-yl | 16.1 | 1.4 | 1.8 |
| IV-1 | hydrogen | 30.2 | 21.9 | 13.8 |
| IV-2 | methyl | 21.1 | 17.3 | 14.6 |
| IV-3 | ethyl | 10.6 | 17.1 | 15.4 |
| IV-4 | isopentyl | 30.8 | 17.6 | 13.5 |

Basing on the data in table 1, it is concluded that the oxime derivataives in the present invention showed good growth inhibition activities on tested DU145, MCF-7 and K562 cells, and they can be used for the preparation of anticancer drugs.

Example 3

This example involves a series of racemic shikonin oxime compounds by way of the methylation of hydroxyl and the oximation of carbonyl groups on the naphthazarin ring. The general structures of these oxime compounds are shown as V and VI:

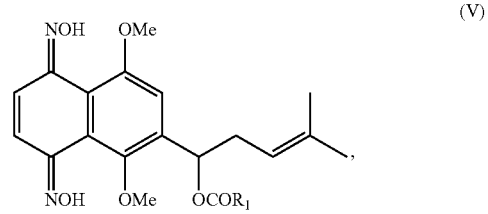

(V)

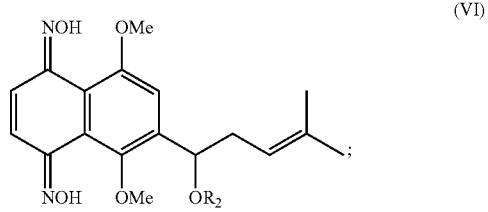

(VI)

R$_1$ and R$_2$ were defined in table 2.

Figure 7:
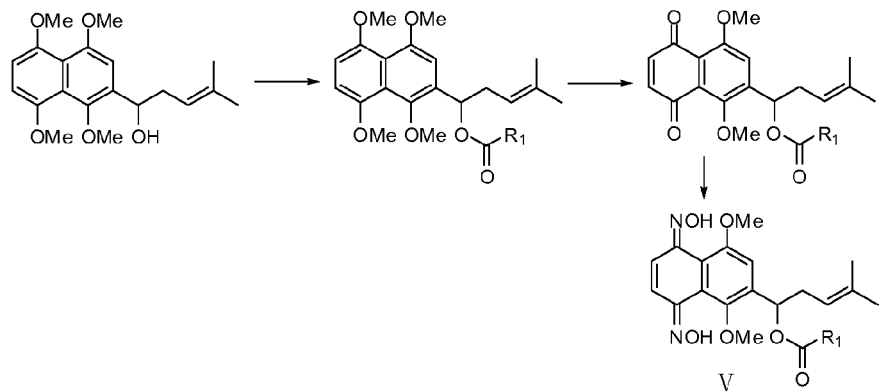
FIG. 7 illustrates a synthetic method of racemic naphthazarin parent nucleus hydroxyl methylation carbonyl oxime ester derivative (Formula V).

1. The Preparation of Ester Derivatives Named as Series of V:

The synthetic routes on compounds I and III were showed respectively in FIG. 7. (±)-1,4,5,8-tetramethoxyshikonin, whose synthetic route was shown in FIG. 9, was used as starting material (the specific preparation methods refer to the patent ZL200510025243.1).

To (±)-4-methyl-1-(1,4,5,8-tetramethxynaphthalen-2-yl) pent-3-en-1-ol in dry CH2Cl2 was added carboxylic acid (1.2-2equivalent), DCC (1.5-5 equivalent) and DMAP (0.1 equivalent) and the mixture was stirred for 2-12 h at room temperature. After the completion of reaction, the precipitate was removed by filtration. To the filtrate was added CAN (5-10 equivalent) in water (10 mL) and the mixture was stirred at 0-5° C. After 10-20 minutes, the reaction was extracted with DCM and the combined extracts were dried over anhydrous sodium sulfate and concentrated. The residue was purified by silica gel column chromatography to give yellow oily compounds. Stirring of obtained yellow oily compounds and hydroxylamine hydrochloride (2.2-4 equivalent) respectively in dry ethanol with the presence of pyridine (2.5-6 equivalent) produced oxime compounds V (shown in table 2).

For the synthesis of V-1, 1.5 equivalent DCC, 1.2 equivalent acetic acid, 3 equivalent CAN, 2.2 equivalent hydroxylamine hydrochloride and 2.5 equivalent dry pyridine were used. For the synthesis of V-2, 5 equivalent DCC, 2 equivalent 3-methylbutanoic acid, 8 equivalent CAN, 4 equivalent hydroxylamine hydrochloride and 6 equivalent dry pyridine were used. For the synthesis of V-3, 3 equivalent DCC, 1.5equivalent 3-hydroxy-3-methylbutanoicacid, 5 equivalent CAN, 3.5 equivalent hydroxylamine hydrochloride and 5 equivalent dry pyridine were used. For the synthesis of V-4-V-16, 1.5 equivalent DCC, 1.2 equivalent carboxylic acid, 3 equivalent CAN, 2.2 equivalent hydroxylamine hydrochloride and 2.5 equivalent dry pyridine were used.

Figure 8:
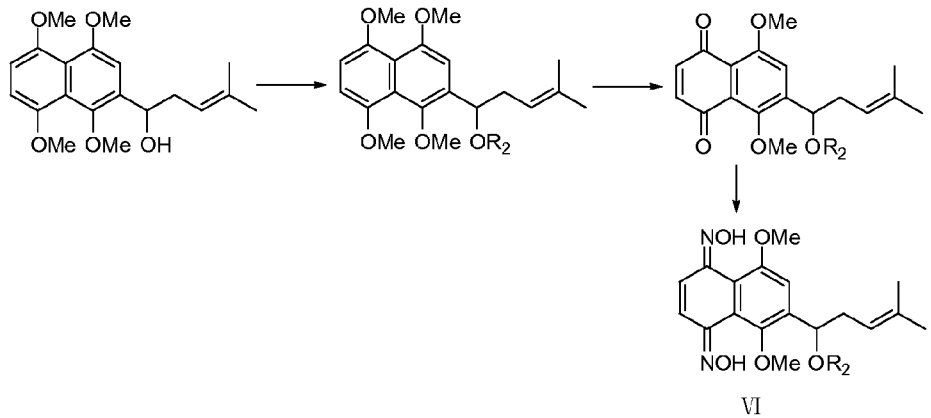
FIG. 8 illustrates a synthetic method of racemic naphthazarin parent nucleus hydroxyl methylation carbonyl oxime ether derivative (Formula VI).
Figure 9:
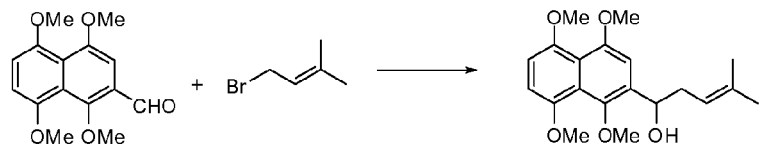
FIG. 9 illustrates a synthetic method of (±)1,4,5,8-tetramethoxyshikonin.

2. The Preparation of Ether Derivatives Named as Series VI:

The scheme for the synthesis of ether compounds VI was regarded as FIG. 8, while the synthesis of (±)-1,4,5,8-tetramethoxyshikonin was shown in FIG. 9.

To a solution of (R)- or (S)-4-methyl-1-(1,4,5,8-tetramethoxynaphthalen-2-yl)pent-3-en-1-ol in dry DMF at 0° C. was added NaH (2-5 equivalent) and the mixture was stirred for 0.5 h at 0° C. Then alkyl halide (1.2-4 equivalent) was added and the reaction mixture was allowed to stir at room temperature for 12-24 h. After the completion of the reaction, the reaction was extracted with ethyl acetate and the extracts were concentrated. The residue was dissolved in DCM and a solution of CAN (3-8 equivalent) in water was added and stirred for 10-20 minutes at 0° C. Then the organic phase was extracted with DCM and purified by silica gel column chromatography to collect yellow oily compounds, which were converted into ether oxime compounds by the condensation reaction with hydroxylamine hydrochloride (2.2-4 equivalent) in dry ethanol with the presence of pyridine(2.5-6 equivalent).

For the synthesis of VI-1, 3 equivalent CAN, 2.2 equivalent hydroxylamine hydrochloride and 2.5 equivalent dry pyridine were used. For the synthesis of VI-2, 5 equivalent NaH, 4 equivalent iodomethane, 8 equivalent CAN, 4 equivalent hydroxylamine hydrochloride and 6 equivalent dry pyridine were used. For the synthesis of VI-3, 3 equivalent NaH, 2.2 equivalent bromoethane, 5 equivalent CAN, 3 equivalent hydroxylamine hydrochloride and 4.5 equivalent dry pyridine were used. For the synthesis of VI-4, 4 equivalent NaH, 3 equivalent 1-bromo-3-methylbutane, 6 equivalent CAN, 3.5 equivalent hydroxylamine hydrochloride and 5 equivalent dry pyridine were used.

3. The Spectral Characterization of Compounds V and VI:

1-((5E,8E)-5,8-bis(hydroxyimino)-1,4-dimethoxy-5,8-dihydronaphthalen-2-yl)-4-methylpent-3-en-1-yl acetate (V-1): yield 86%, $^1$H-NMR (300 MHz, DMSO): δ=12.08 (s, 2H, $H_{N-OH}$), 7.38 (s, 2H, $H_{Quin}$), 7.04 (s, 1H, $H_{Ar}$), 6.02 (t, J=6.3 Hz, 1H, ArCH—), 5.12 (t, J=6.3 Hz, 1H, —CH═), 3.80 (s, 3H, ArOCH$_3$), 3.64 (s, 3H, ArOCH$_3$), 2.49 (d, J=1.5 Hz, 2H, —CH$_2$—), 2.08 (s, 3H, —COCH$_3$), 1.64 (s, 3H, —CH$_3$), 1.54 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 3-methylbut-2-enoate (V-2): yield 80%, $^1$H-NMR (300 MHz, DMSO): δ=12.06 (s, 2H, $H_{N-OH}$), 7.36 (s, 2H, $H_{Quin}$), 7.00 (s, 1H, $H_{Ar}$), 6.04 (t, J=6.2 Hz, 1H, ArCH—), 5.78 (s, 1H, —COCH═C—), 5.10 (s, 1H, —CH$_2$CH═C), 3.74 (s, 3H, ArOCH$_3$), 3.64 (s, 3H, ArOCH$_3$), 2.48 (t, J=1.8 Hz, 2H, —CH$_2$—), 2.08 (s, 3H, —CH═CCH$_3$), 1.86 (s, 3H, —CH═CCH$_3$), 1.60 (s, 3H, —CH$_3$), 1.52 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 3-hydroxy-3-methylbutanoate (V-3): yield 75%, $^1$H-NMR (300 MHz, DMSO): δ=12.09 (s, 2H, $H_{N-OH}$), 7.39 (s, 2H, $H_{Quin}$), 7.11 (s, 1H, $H_{Ar}$), 6.01 (t, J=6.6 Hz, 1H, ArCH—), 5.17-5.13 (m, 1H, —CH═), 4.64 (s, 1H, —CHOH), 3.79 (s, 3H, ArOCH$_3$), 3.67 (s, 3H, ArOCH$_3$), 2.55-2.43 (m, 4H, —CH$_2$—), 1.65 (s, 3H, —CH═CCH$_3$), 1.55 (s, 3H, —CH═CCH$_3$), 1.24 (s, 3H, —CH$_3$), 1.19 (s, 3H, —CH$_3$).

1-((5E,8E)-5,8-bis(hydroxyimino)-1,4-dimethoxy-5,8-dihydronaphthalen-2-yl)-4-methylpent-3-en-1-yl isobutyrate (V-4): yield 72%, $^1$H-NMR (300 MHz, DMSO): δ=12.06 (s, 2H, $H_{N-OH}$), 7.36 (s, 2H, $H_{Quin}$), 7.00 (s, 1H, $H_{Ar}$), 6.00 (t, J=6.6 Hz, 1H, ArCH—), 5.12 (s, 1H, —CH═), 3.76 (s, 3H, ArOCH$_3$), 3.64 (s, 3H, ArOCH$_3$), 2.66-2.50 (m, 3H, —COCH— and ═CCH$_2$—), 1.64 (s, 3H, —CH═CCH$_3$), 1.54 (s, 3H, —CH═CCH$_3$), 1.11 (s, 3H, —CH$_3$), 1.10 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 3-methylbutanoate (V-5): yield 83%, $^1$H-NMR (300 MHz, DMSO): δ=12.07 (s, 2H, $H_{N-OH}$), 7.37 (s, 2H, $H_{Quin}$), 7.02 (s, 1H, $H_{Ar}$), 6.04 (t, J=7.2 Hz, 1H, ArCH—), 5.14 (d, J=6.0 Hz, 1H, —CH═), 3.77 (s, 3H, ArOCH$_3$), 3.65 (s, 3H, ArOCH$_3$), 2.48 (s, 2H, —CH$_2$—), 2.25 (d, J=7.2 Hz, 2H, —CH$_2$—), 2.0 (m, 1H, —CH—), 1.62 (s, 3H, —CH═CCH$_3$), 1.54 (s, 3H, —CH═CCH$_3$), 0.89 (s, 3H, —CH$_3$), 0.87 (s, 3H, —CH$_3$).

1-((5E,8E)-5,8-bis(hydroxyimino)-1,4-dimethoxy-5,8-dihydronaphthalen-2-yl)-4-methylpent-3-en-1-yl propionate (V-6): yield 76%,$^1$H-NMR (400 MHz, DMSO): δ=12.08 (s, 2H, $H_{N-OH}$), 7.38 (s, 2H, $H_{Quin}$), 7.03 (s, 1H, $H_{Ar}$), 6.04 (t, J=6.0 Hz, 1H, ArCH—), 5.13 (t, J=6.4 Hz, 1H, —CH═), 3.79 (s, 3H, ArOCH$_3$), 3.66 (s, 3H, ArOCH$_3$), 2.50-2.37 (m, 4H, —CH$_2$—), 1.64 (s, 3H, —CH═CCH$_3$), 1.55 (s, 3H, —CH═CCH$_3$), 1.05 (t, J=7.2 Hz, 3H, —CH$_3$).

1-((5E,8E)-5,8-bis(hydroxyimino)-1,4-dimethoxy-5,8-dihydronaphthalen-2-yl)-4-methylpent-3-en-1-yl methacrylate (V-7): yield 74%, $^1$H-NMR (400 MHz, DMSO): δ=12.09 (s, 2H, $H_{N-OH}$), 7.38 (s, 2H, $H_{Quin}$), 7.05 (s, 1H, $H_{Ar}$), 6.15 (s, 1H, —C═CH$_2$), 6.10 (dd, J=7.2, 5.6 Hz, 1H, —C═CH$_2$), 5.73 (s, 1H, ArCH—), 5.12 (t, 1H, J=6.8 Hz, —CH$_2$C═), 3.75 (s, 3H, ArOCH$_3$), 3.66 (s, 3H, ArOCH$_3$), 2.61-2.54 (m, 2H, —CH$_2$—), 1.91 (s, 3H, —CH$_2$═CCH$_3$), 1.63 (s, 3H, —CH$_3$), 1.55 (s, 3H, —CH$_3$).

1-((5E,8E)-5,8-bis(hydroxyimino)-1,4-dimethoxy-5,8-dihydronaphthalen-2-yl)-4-methylpent-3-en-1-yl benzoate (V-8): yield 75%, $^1$H-NMR (400 MHz, DMSO): δ=12.10 (s, 2H, $H_{N-OH}$), 8.06 (d, J=6.8 Hz, 2H, $H_{Quin}$), 7.70-7.39 (m, 5H, H$_{Ar}$), 7.19 (s, 1H, H$_{Ar}$), 6.30 (t, J=6.0 Hz, 1H, ArCH—), 5.20 (s, 1H, =CH—), 3.75 (s, 3H, ArOCH$_3$), 3.71 (s, 3H, ArOCH$_3$), 2.72-2.63 (m, 2H, —CH$_2$—), 1.64 (s, 3H, —CH$_3$), 1.59 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 2-fluorobenzoate (V-9): yield 73%, $^1$H-NMR (400 MHz, DMSO): δ=12.10 (s, 2H, H$_{N—OH}$), 7.97 (dd, J=7.6, 6.4 Hz, 1H, H$_{Ar}$), 7.71-7.67 (m, 1H, H$_{Ar}$), 7.41-7.36 (m, 4H, H$_{Ar}$ and H$_{Quin}$), 7.19 (s, 1H, ArH), 6.31 (t, J=5.6 Hz, 1H, ArCH—), 5.21 (t, J=6.8 Hz, 1H, =CH—), 3.78 (s, 3H, ArOCH$_3$), 3.72 (s, 3H, ArOCH$_3$), 2.69-2.61 (m, 2H, —CH$_2$—), 1.66 (s, 3H, —CH$_3$), 1.56 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 4-fluorobenzoate (V-10): yield 80%, $^1$H-NMR (400 MHz, DMSO): δ=12.10 (s, 2H, H$_{N—OH}$), 8.12 (dd, J=8.4, 5.6 Hz, 2H, H$_{Quin}$), 7.39-7.35 (m, 4H, H$_{Ar}$), 7.19 (s, 1H, H$_{Ar}$), 6.31-6.28 (m, 1H, ArCH—), 5.20 (t, J=2.0 Hz, 1H, =CH—), 3.76 (s, 3H, ArOCH$_3$), 3.70 (s, 3H, ArOCH$_3$), 2.74-2.61 (m, 2H, —CH$_2$—), 1.63 (s, 3H, —CH$_3$), 1.58 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 2-chlorobenzoate (V-11): yield 81%, $^1$H-NMR (400 MHz, DMSO): δ=12.11 (s, 2H, N$_{N—OH}$), 7.87 (d, J=7.6 Hz, 1H, H$_{Ar}$), 7.60 (d, J=3.6 Hz, 2H, H$_{Ar}$), 7.52-7.48 (m, 1H, H$_{Ar}$), 7.40 (s, 2H, H$_{Quin}$), 7.18 (s, 1H, H$_{Ar}$), 6.30 (t, J=5.6 Hz, 1H, ArCH—), 5.21 (s, 1H, =CH—), 3.77 (s, 3H, ArOCH$_3$), 3.71 (s, 3H, ArOCH$_3$), 2.69-2.63 (m, 2H, —CH$_2$—), 1.65 (s, 3H, —CH$_3$), 1.56 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 4-chlorobenzoate (V-12): yield 83%, $^1$H-NMR (400 MHz, DMSO): δ=12.11 (s, 2H, N$_{N—OH}$), 8.08 (d, J=8.4 Hz, 2H, H$_{Ar}$), 7.63 (d, J=8.4 Hz, 2H, H$_{Ar}$), 7.40 (s, 2H, H$_{Quin}$), 7.19 (s, 1H, H$_{Ar}$), 6.31 (t, J=5.6 Hz, 1H, ArCH—), 5.20 (s, 1H, —CH=), 3.77 (s, 3H, ArOCH$_3$), 3.71 (s, 3H, ArOCH$_3$), 2.73-2.64 (m, 2H, —CH$_2$—), 1.65 (s, 3H, —CH$_3$), 1.60 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 4-methoxybenzoate (V-13): yield 86%, $^1$H-NMR (400 MHz, DMSO): δ=12.10 (s, 2H, H$_{NOH}$), 8.01 (d, J=4.8 Hz, 2H, H$_{Ar}$), 7.39 (s, 2H, H$_{Quin}$), 7.07 (d, J=8.8 Hz, 2H, H$_{Ar}$), 6.26 (t, J=5.6 Hz, 1H, ArCH—), 5.20 (s, 1H, =CH—), 3.84 (s, 3H, ArOCH$_3$), 3.74 (s, 3H, ArOCH$_3$), 3.70 (s, 3H, ArOCH$_3$), 2.70-2.59 (m, 2H, —CH$_2$—), 1.64 (s, 3H, —CH$_3$), 1.58 (s, 3H, —CH$_3$).

1-((5E,8E)-5,8-bis(hydroxyimino)-1,4-dimethoxy-5,8-dihydronaphthalen-2-yl)-4-methylpent-3-en-1-yl 4-nitrobenzoate (V-14): yield 82%, $^1$H-NMR (400 MHz, DMSO): δ=12.11 (s, 2H, H$_{N—OH}$), 8.12 (d, J=24.8 Hz, 4H, H$_{Ar}$), 7.39 (s, 2H, H$_{Quin}$), 7.21 (s, 1H, H$_{Ar}$), 6.34 (s, 1H, ArCH—), 5.20 (s, 1H, =CH—), 3.77 (s, 3H, ArOCH$_3$), 3.71 (s, 3H, ArOCH$_3$), 2.75-2.68 (m, 2H, —CH$_2$—), 1.63 (s, 3H, —CH$_3$), 1.59 (s, 3H, —CH$_3$).

1-((5E,8E)-5,8-bis(hydroxyimino)-1,4-dimethoxy-5,8-dihydronaphthalen-2-yl)-4-methylpent-3-en-1-yl picolinate (V-15): yield 78%, $^1$H-NMR (400 MHz, DMSO): δ=12.07 (s, 2H, H$_{N—OH}$), 8.73 (d, J=4.4 Hz, 1H, H$_{Py}$), 8.10 (d, J=8.0 Hz, 1H, H$_{Py}$), 8.01-8.00 (m, 1H, H$_{Py}$), 7.66-7.60 (m, 1H, H$_{Py}$), 7.37 (s, 2H, H$_{Quin}$), 7.20 (s, 1H, H$_{Ar}$), 6.30 (t, J=6.0 Hz, 1H, ArCH—), 5.18 (t, J=6.8 Hz, 1H, =CH—), 3.73 (s, 3H, ArOCH$_3$), 3.69 (s, 3H, ArOCH$_3$), 2.72-2.67 (m, 2H, —CH$_2$—), 1.63 (s, 3H, —CH$_3$), 1.59 (s, 3H, —CH$_3$).

1-((5E,8E)-5,8-bis(hydroxyimino)-1,4-dimethoxy-5,8-dihydronaphthalen-2-yl)-4-methylpent-3-en-1-yl thiophene-2-carboxylate (V-16): yield 76%, $^1$H-NMR (400 MHz, DMSO): δ=12.12 (s, 2H, H$_{N—OH}$), 7.98 (d, J=2.8 Hz, 1H, H$_{Thiophene}$), 7.91 (d, J=2.4 Hz, 1H, H$_{Thiophene}$), 7.40 (s, 2H, H$_{Quin}$), 7.25 (t, J=4.4 Hz, 1H, H$_{Thiophene}$), 7.16 (s, 1H, H$_{Ar}$), 6.25-6.21 (m, 1H, ArCH—), 5.19 (t, J=6.0 Hz, 1H, =CH—), 3.77(s, 3H, ArOCH$_3$), 3.70 (s, 3H, ArOCH$_3$), 2.72-2.57 (m, 2H, —CH$_2$—), 1.65 (s, 3H, —CH$_3$), 1.60 (s, 3H, —CH$_3$).

(1E,4E)-6-(1-hydroxy-4-methylpent-3-en-1-yl)-5,8-dimethoxynaphthalene-1,4-dione dioxime (VI-1): yield 83%, $^1$H-NMR (400 MHz, DMSO): δ=12.02(s, 2H, H$_{N—OH}$), 7.39 (s, 2H, H$_{Quin}$), 7.26 (s, 1H, H$_{Ar}$), 5.27 (s, 1H, =CH—), 4.96 (dd, J=7.6, 4.8 Hz,1H, ArCH—), 3.80 (s, 3H, ArOCH$_3$), 3.61 (s, 3H, OCH$_3$), 2.44-2.22 (m, 2H, —CH$_2$—), 1.66 (s, 3H, —CH$_3$), 1.53 (s, 3H, —CH$_3$).

(1E,4E)-5,8-dimethoxy-6-(1-methoxy-4-methylpent-3-en-1-yl)naphthalene-1,4-dione dioxime (VI-2): yield 85%, $^1$H-NMR (300 MHz, DMSO): δ=12.04 (s, 2H, H$_{N—OH}$), 7.39 (s, 2H, H$_{Quin}$), 7.04 (s, 1H, H$_{Ar}$), 5.19 (t, J=6.9 Hz, 1H, —CH=), 4.59 (t, J=6.3 Hz, 1H, ArCH—), 3.78 (s, 3H, ArOCH$_3$), 3.59 (s, 3H, ArOCH$_3$), 3.17 (s, 3H, —OCH$_3$), 2.35 (t, J=6.3 Hz, 2H, —CH$_2$—), 1.63 (s, 3H, —CH$_3$), 1.49 (s, 3H, —CH$_3$).

(1E,4E)-6-(1-ethoxy-4-methylpent-3-en-1-yl)-5,8-dimethoxynaphthalene-1,4-dione dioxime (VI-3): yield 89%, $^1$H-NMR (400 MHz, DMSO): δ=12.02 (s, 2H, H$_{N—OH}$), 7.38 (s, 2H, H$_{Quin}$), 7.09 (s, 1H, H$_{Ar}$), 5.20 (t, J=5.6 Hz, 1H, =CH—), 4.68 (t, J=6.8 Hz, 1H, ArCH—), 3.78 (s, 3H, ArOCH$_3$), 3.59 (s, 3H, ArOCH$_3$), 3.37-3.32 (m, 2H, —OCH$_2$CH$_3$), 2.36-2.35 (m, 2H, =CHCH$_2$—), 1.64 (s, 3H, =CCH$_3$), 1.50 (s, 3H, =CCH$_3$), 1.20 (t, J=6.8 Hz, 3H, —CH$_3$).

(1E,4E)-6-(1-(isopentyloxy)-4-methylpent-3-en-1-yl)-5,8-dimethoxynaphthalene-1,4-dione dioxime (VI-4): yield 77%, $^1$H-NMR (400 MHz, DMSO): δ=12.02 (s, 2H, H$_{NOH}$), 7.38 (d, J=2.8 Hz, 2H, H$_{Quin}$), 7.08 (s, 1H, H$_{Ar}$), 5.21 (t, J=6.8 Hz, 1H, ArCH—), 4.65 (t, J=6.8 Hz, 1H, =CH—), 3.78 (s, 3H, ArOCH$_3$), 3.60 (s, 3H, ArOCH$_3$), 3.31 (t, J=6.0 Hz, 2H, —CH$_2$O—), 2.35-2.32 (m, 2H, =CHCH$_2$—), 1.75-1.68 (m, 1H, —CH(CH$_3$)$_2$), 1.64 (s, 3H, =CCH$_3$), 1.51 (s, 3H, =CCH$_3$), 1.44-1.38 (m, 2H, —CH$_2$CH(CH$_3$)$_2$), 0.87 (d, J=6.8 Hz, 3H, —CH$_3$), 0.82 (d, J=6.8 Hz, 3H, —CH$_3$).

Example 4

The in vitro cytotoxicities of the prepared racemic shikonin oxime derivatives in example 3 were evaluated against MCF-7 (breast cancer), K562 (leukemia) and DU145 (prostate cancer) cells by the standard MTT assay. Antitumor potential of these compounds was displayed as IC$_{50}$ values that were calculated by linear regression analysis of the concentration-response curves afforded for each compound. The results are summarized in Table 2.

TABLE 2

In vitro inhibitory activity of racemic shikonin derivatives against DU145, MCF-7 and K562 cells

| Compds. | R (R$_1$ or R$_2$) | IC$_{50}$ (DU145) | IC$_{50}$ (MCF-7) | IC$_{50}$ (K562) |
|---|---|---|---|---|
| V-1 | methyl | 24.2 | 14.7 | 7.3 |
| V-2 | 3-methylbut-2-enyl | 10.3 | 3.6 | 1.5 |
| V-3 | 3-hydroxyisobutyl | 29.9 | 15.8 | 6.5 |
| V-4 | isopropyl | 9.3 | 4.0 | 3.3 |
| V-5 | isobutyl | 17.8 | 12.7 | 1.3 |
| V-6 | ethyl | 12.6 | 5.3 | 5.0 |
| V-7 | methylvinyl | 10.3 | 3.6 | 3.2 |
| V-8 | phenyl | 19.4 | 3.5 | 1.9 |

TABLE 2-continued

In vitro inhibitory activity of racemic shikonin derivatives against DU145, MCF-7 and K562 cells

| Compds. | R ($R_1$ or $R_2$) | $IC_{50}$ (DU145) | $IC_{50}$ (MCF-7) | $IC_{50}$ (K562) |
|---|---|---|---|---|
| V-9 | 2-fluorophenyl | 20.9 | 4.7 | 1.8 |
| V-10 | 4-fluorophenyl | 18.2 | 3.3 | 1.5 |
| V-11 | 2-chlorophenyl | 18.0 | 4.0 | 2.0 |
| V-12 | 4-chlorophenyl | 15.8 | 4.6 | 1.5 |
| V-13 | 4-methoxyphenyl | 16.0 | 3.3 | 1.8 |
| V-14 | 4-nitrophenyl | 10.7 | 1.9 | 2.5 |
| V-15 | pyridin-2-yl | 12.4 | 8.8 | 3.9 |
| V-16 | thiophen-2-yl | 16.6 | 4.7 | 2.0 |
| VI-1 | hydrogen | 55.4 | 40.4 | 30.7 |
| VI-2 | methyl | 32.4 | 25.2 | 19.1 |
| VI-3 | ethyl | 17.1 | 15.7 | 17.1 |
| VI-4 | isopentyl | 26.3 | 16.2 | 15.4 |

Basing on the data in table 2, it is concluded that the oxime derivataives disclosed in the present invention showed good growth inhibition activities on tested DU145, MCF-7 and K562 cells.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A series of shikonin naphthazarin parent nucleus hydroxyl methylation carbonyl oxime derivatives, as shown in Formula (I) or (II):

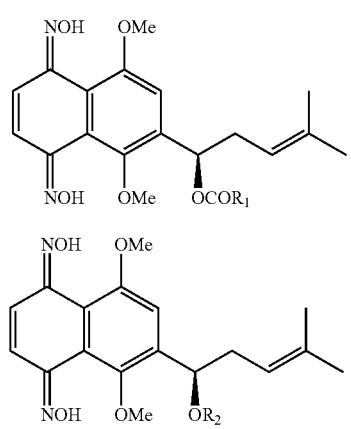

wherein $R_1$ is alkane, olefin, arene, or substituting arene comprising 1 to 6 carbon atoms; and $R_2$ is alkane, olefin, arene, or substituting arene comprising 1 to 6 carbon atoms or is H.

2. The shikonin naphthazarin parent nucleus hydroxyl methylation carbonyl oxime derivatives, as described in claim 1, wherein $R_1$ is methyl, isopropyl, isobutyl, 2-hydroxyl-2-methylpropyl, phenyl, 2-fluorophenyl, 4-fluorophenyl, 1-methylethylene, 2-clorophenyl, 4-clorophenyl, 4-methoxyphenyl, ethylene, 2-thiophenyl, 4-nitrophenyl or 2-pyridyl; $R_2$ is hydrogen, methyl, ethyl or isopentyl.

3. A series of alkannin naphthazarin parent nucleus hydroxyl methylation carbonyl oxime derivatives, as shown in Formula (III) or (IV):

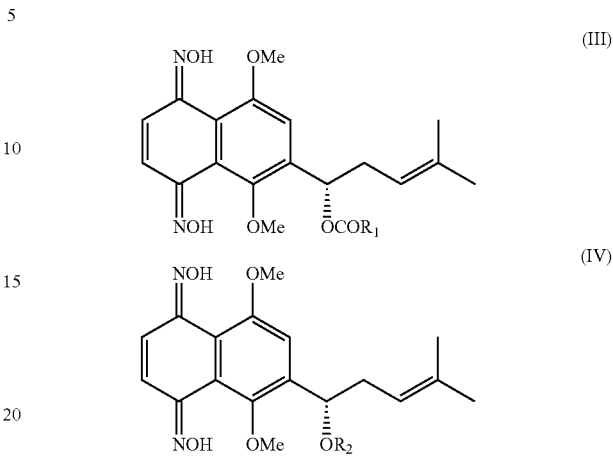

wherein R1 is alkane, olefin, arene, or substituting arene comprising 1 to 6 carbon atoms; and R2 is alkane, olefin, arene, or substituting arene comprising 1 to 6 carbon atoms or is H.

4. The alkannin naphthazarin parent nucleus hydroxyl methylation carbonyl oxime derivatives, as described in claim 3, wherein $R_1$ is methyl, isopropyl, isobutyl, 2-hydroxyl-2-methylpropyl, phenyl, 2-fluorophenyl, 4-fluorophenyl, 1-methylethylene, 2-clorophenyl, 4-clorophenyl, 4-methoxyphenyl, ethylene, 2-thiophenyl, 4-nitrophenyl or 2-pyridyl; $R_2$ is hydrogen, methyl, ethyl or isopentyl.

5. A series of racemic naphthazarin parent nucleus hydroxyl methylation carbonyl oxime derivatives, as shown in Formula (V) or (VI):

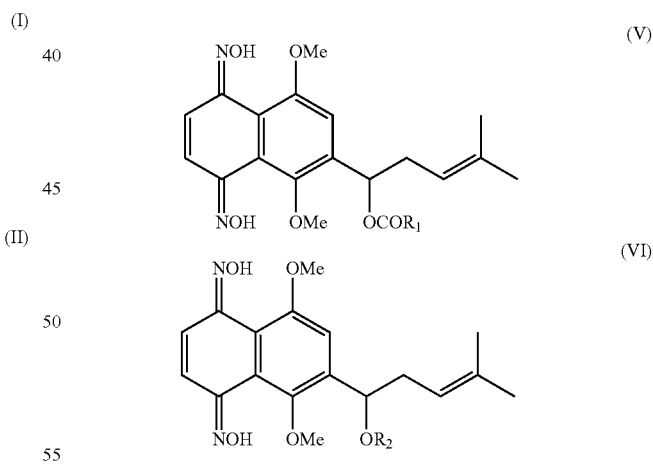

wherein R1 is alkane, olefin, arene, or substituting arene comprising 1 to 6 carbon atoms; and R2 is alkane, olefin, arene, or substituting arene comprising 1 to 6 carbon atoms or is H.

6. The racemic naphthazarin parent nucleus hydroxyl methylation carbonyl oxime derivatives, as described in claim 5, wherein $R_1$ is methyl, isopropyl, isobutyl, 2-hydroxyl-2-methylpropyl, phenyl, 2-fluorophenyl, 4-fluorophenyl, 1-methylethylene, 2-clorophenyl, 4-clorophenyl, 4-methoxyphenyl, ethylene, 2-thiophenyl, 4-nitrophenyl or 2-pyridyl; $R_2$ is hydrogen, methyl, ethyl or isopentyl.

7. A method for preparing antitumor drugs, comprising applying the shikonin naphthazarin parent nucleus hydroxyl methylation carbonyl oxime derivatives as described in claim 1.

8. A method for preparing antitumor drugs, comprising applying the alkannin naphthazarin parent nucleus hydroxyl methylation carbonyl oxime derivatives as described in claim 3.

9. A method for preparing antitumor drugs, comprising applying the racemic naphthazarin parent nucleus hydroxyl methylation carbonyl oxime derivatives as described in claim 5.

* * * * *